(12) United States Patent
Shores et al.

(10) Patent No.: US 7,658,740 B2
(45) Date of Patent: Feb. 9, 2010

(54) SURGICAL ATTACHMENT INSTRUMENT AND METHOD

(75) Inventors: Rex W. Shores, The Colony, TX (US);
Paul A. Cihak, Grapevine, TX (US);
Allen P. Hilton, Arlington, TX (US)

(73) Assignee: Medtronic, Inc., Minneapolis, MN (US)

( * ) Notice: Subject to any disclaimer, the term of this patent is extended or adjusted under 35 U.S.C. 154(b) by 1013 days.

(21) Appl. No.: 10/919,745

(22) Filed: Aug. 17, 2004

(65) Prior Publication Data
US 2006/0041268 A1  Feb. 23, 2006

(51) Int. Cl.
*A61B 5/00* (2006.01)
(52) U.S. Cl. .................................. 606/86 R; 606/80
(58) Field of Classification Search ............ 606/79, 606/80, 81, 86 R, 96, 86 A, 86 B, 167
See application file for complete search history.

(56) References Cited
U.S. PATENT DOCUMENTS 5,893,851 A * 4/1999 Umber et al. ............... 606/80
5,941,891 A * 8/1999 Walen ...................... 606/167
5,993,453 A * 11/1999 Bullara et al. .............. 606/79

OTHER PUBLICATIONS

Midas Rex Instrumentation System Instruction Manual; "Midas Rex Classic System" and "Midas Rex III System"; Medtronic Midas Rex 2000, 23 pages.
www.medtronic.com/neuro/midasrex/toolsweb.html; "Dissecting Tools for Legend"; Version C3.01 Medtronic, Inc. 2004; two pages.
www.Medtronic.com/neuro/midasrex/straight.html; "Legend Straight Attachments"; Version C3.01 Medtronic, Inc. 2004; two pages.

* cited by examiner

*Primary Examiner*—Thomas C Barrett
*Assistant Examiner*—Michael J Araj
(74) *Attorney, Agent, or Firm*—Haynes and Boone LLP (57) ABSTRACT

A surgical attachment instrument and method according to which a housing is adapted to be coupled to a motor. A tubular member is coupled to the housing so that an end of the tubular member extends from the housing at a predetermined distance. The predetermined distance may be selectively adjusted by a repeatable increment.

53 Claims, 10 Drawing Sheets

SURGICAL ATTACHMENT INSTRUMENT AND METHOD

FIELD OF THE INVENTION

The present invention relates generally to surgical instruments and in particular to surgical instruments for dissecting bone and other tissue.

BACKGROUND

During various surgical procedures, it is necessary to dissect bone or other tissue. Many conventional surgical instruments used for the dissection of bone or other tissue employ pneumatic or electrical motors to rotate a cutting element. In their most basic form, such surgical instruments typically include a motor having a rotary shaft, a dissection tool having a cutting or abrading element that is moved by the rotating shaft of the motor, and a coupling arrangement for connecting the dissection tool to the rotary shaft. The dissection tool often has a small shaft diameter in relation to its length. The shaft may bend or flail in use if not adequately supported or protected. The risk of bending is heightened when the shaft is used with a motor that is designed to reach speeds in excess of 72,000 rpm.

To support and/or protect a dissection-tool shaft, an attachment or tube may be provided that engages the motor and receives a portion of the dissection-tool shaft. Some attachments or tubes may remain stationary relative to the motor. An example of a stationary attachment is disclosed in detail in co-pending patent application Ser. No. 10/200,683, filed Jul. 22, 2002, the disclosure of which is incorporated by reference.

Other attachments or tubes may move axially or telescope relative to the motor, thereby allowing the surgeon to vary the distance that the distal end of the tube extends from the motor, and hence vary the distance that the distal end of the dissection-tool shaft extends from the distal end of the tube. Thus, the portion of the dissection-tool shaft received and supported and/or protected by the tube may be varied as desired or needed. For example, a decrease in the portion of the dissecting-tool shaft received by the tube may be required to accommodate spatial constraints associated with the surgical area. An example of a telescoping attachment is disclosed in detail in co-pending patent application Ser. No. 10/326,178, filed Dec. 20, 2002, the disclosure of which is incorporated by reference.

However, problems may arise during the operation of a surgical instrument having a typical attachment or tube. For example, the stiffness of the tube may not be sufficient to provide adequate stability to the cutting or abrading element, especially in light of the dissection-tool shaft being subjected to various static and/or dynamic loads during normal dissection operation. Also, due in part to vibration, any threadably engaged components of the attachment may disengage from each other during normal dissection operation.

In addition to the foregoing, for telescoping attachments, many configurations require one or more components to be added to the attachment to provide the telescoping functionality. These components may interfere with the surgeon's line of sight to the surgical area during the dissection operation. Also, it may be difficult for the surgeon to telescope the attachment in an incremental and repeatable manner.

Therefore, what is needed is a surgical attachment instrument that overcomes one or more of the above-described problems.

TABLE 1

| United States Patent Publication No. | Publication Date | Inventor | application Ser. No. |
|---|---|---|---|
| 2002/0151902 | Feb. 17, 2002 | Riedel et al. | 10/102,762 |
| 2002/0165549 | Nov. 7, 2002 | Owusu-Akyaw et al. | 10/135,608 |
| 2003/0023256 | Jan. 30, 2003 | Estes et al. | 10/200,683 |
| 2003/0163134 | Aug. 28, 2003 | Riedel et al. | 10/164,867 |
| 2003/0229351 | Dec. 11, 2003 | Tidwell et al. | 10/164,880 |
| 2004/0122460 | Jun. 24, 2004 | Shores et al. | 10/326,178 |

All patent publications listed in Table 1 are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patent publications of Table 1 may be modified advantageously by using the teachings of the present invention.

SUMMARY OF THE INVENTION

In one embodiment, a surgical attachment instrument includes a housing adapted to be coupled to a motor. A tubular member is coupled to and extends from the housing at a predetermined distance. The predetermined distance may be adjusted in repeatable increments so that the tubular member telescopes relative to the housing in an incremental and repeatable manner. Further, the tubular member may be locked so that longitudinal movement of the tubular member relative to the housing is prevented. Means for adjusting and locking the tubular member are provided without appreciably increasing the surgical attachment instrument's interference with the surgeon's line of sight to the surgical area.

Further, a coupling connects the tubular member and the housing, and an arcuate member is concentrically disposed between the coupling and the housing. At least a portion of the arcuate member extends in a channel formed in the housing to resist disengagement of the coupling from the housing during operation of the surgical attachment instrument. Still further, the tubular member extends around at least two adjacent bearing assemblies that support a shaft adapted to be coupled to the motor. A spacer extends between the two adjacent bearing assemblies and is lockingly engaged with the tubular member to stabilize the shaft.

Further areas of applicability of the present invention will become apparent from the detailed description provided hereinafter. It is understood that various embodiments of the present invention may overcome one or more of the above-described problems. It is further understood that the detailed description is intended for the purpose of illustration only and is not intended to limit the scope of the invention.

DETAILED DESCRIPTION OF THE PREFERRED EMBODIMENTS

Figure 1:
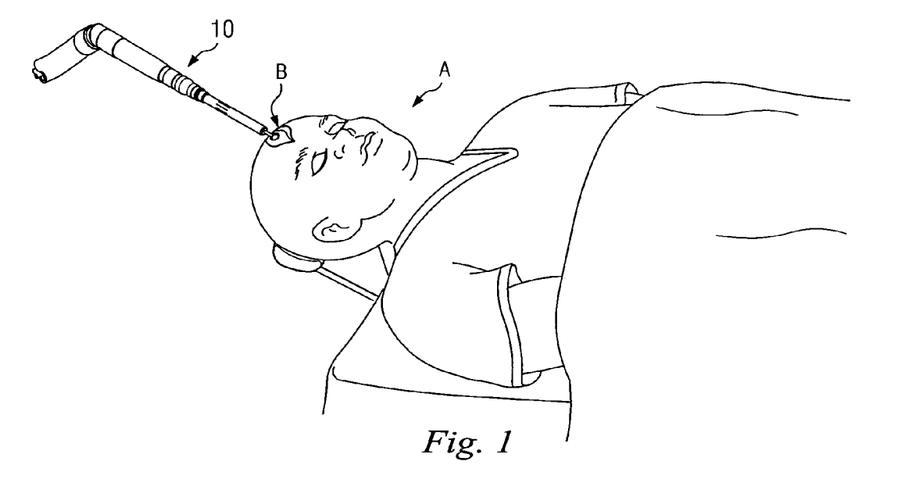
FIG. 1 is an illustration of a dissection tool assembly according to the present invention used in a human patient.

Referring to FIG. 1, the reference numeral 10 refers, in general, to a dissection tool assembly used to dissect human bone or other tissue. For example and as shown, the dissection tool assembly 10 may be used during a neurological operation on a human patient A to dissect a portion of the patient's bone or other tissue B in order to provide access to the brain or other neurological structures.

Figure 2:
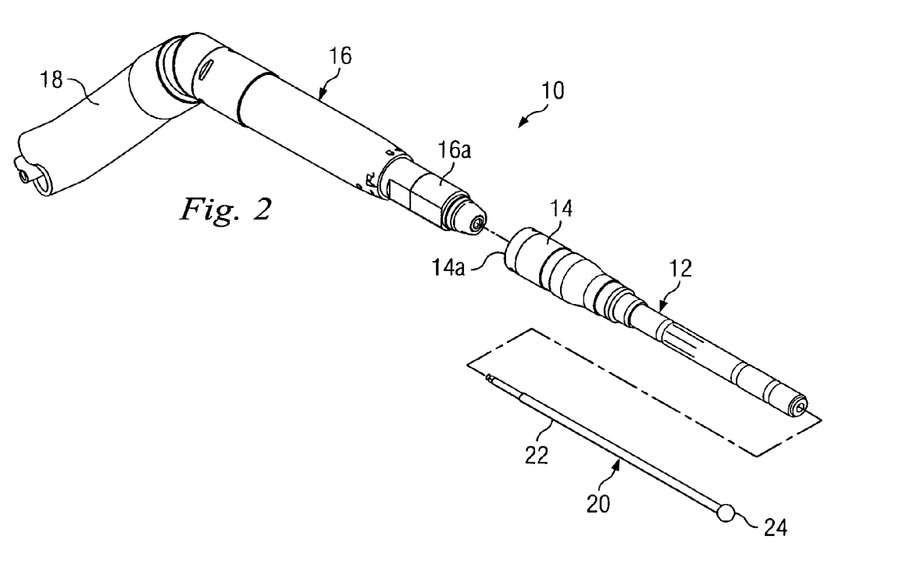
FIG. 2 is a partially exploded view of a dissection tool assembly according to an embodiment.

Referring to FIG. 2, the dissection tool assembly 10 includes a surgical attachment instrument 12 having an attachment housing 14. A pneumatic motor 16 having a distal portion 16a is coupled to a cavity portion 14a formed in the housing 14 so that the distal portion is disposed in the cavity portion. The motor 16 is connected to a hose assembly 18 that supplies pressurized air to the motor and vents low-pressure exhaust air away from the surgical area. The motor 16, the hose assembly 18 and the coupling of the motor 16 to the housing 14 are disclosed in detail in co-pending patent application Ser. No. 10/200,683, filed Jul. 22, 2002, the disclosure of which is incorporated by reference.

A dissection tool 20 includes a shaft 22 and a surgical element such as a dissection head 24 connected to the distal end of the shaft. The shaft 22 is disposed through the surgical attachment instrument 12, and is inserted in and coupled to the distal portion 16a of the motor 16. This coupling of the shaft 22 to the motor 16 is disclosed in detail in the above-incorporated patent application.

Referring to FIGS. 3 through 5D, the surgical attachment instrument 12 further includes a coupling 26 having an external threaded portion 26a and a circumferentially-extending channel 26b formed in the coupling adjacent to the threaded portion. A protrusion 26c extends out of the channel 26b. A ring 26d extends around the coupling 26 and is disposed adjacent to the channel 26b. Opposing through-openings 26e and 26f are formed in the channel 26b. A groove 26g is formed in the proximal end portion of the coupling 26 and a pair of markings 26h and 26i are printed or formed near the distal end of the coupling, the marking 26h indicating a "locked" position and the marking 26i indicating an "unlocked" position, as will be further described. A bore 26j longitudinally extends through the coupling 26.

A tubular member 28 includes a bore 28a and a plurality of grooves 28b formed in the wall of the bore at the proximal end of the tubular member. Transverse index markings 29a through 29e are printed or formed in the tubular member 28. Arrow markings 30a through 30c are also printed or formed in the tubular member 28 perpendicular to and through the index markings 29a through 29e. A plurality of crimps 31a, 31b and 31c are formed in the tubular member 28 so that each crimp includes a protrusion portion extending from the inner wall of the tubular member 28. A plurality of transversely-extending locking channels 32a, 32b, 32c, 32d and 32e are formed in the proximal end portion of the tubular member 28. The longitudinal (or axial) spacing between the channels 32a and 32b, 32b and 32c, 32c and 32d, and 32d and 32e are substantially equal and correspond to the spacing between the index marks 29a and 29b, 29b and 29c, 29c and 29d, and 29d and 29e, respectively.

Figure 4:
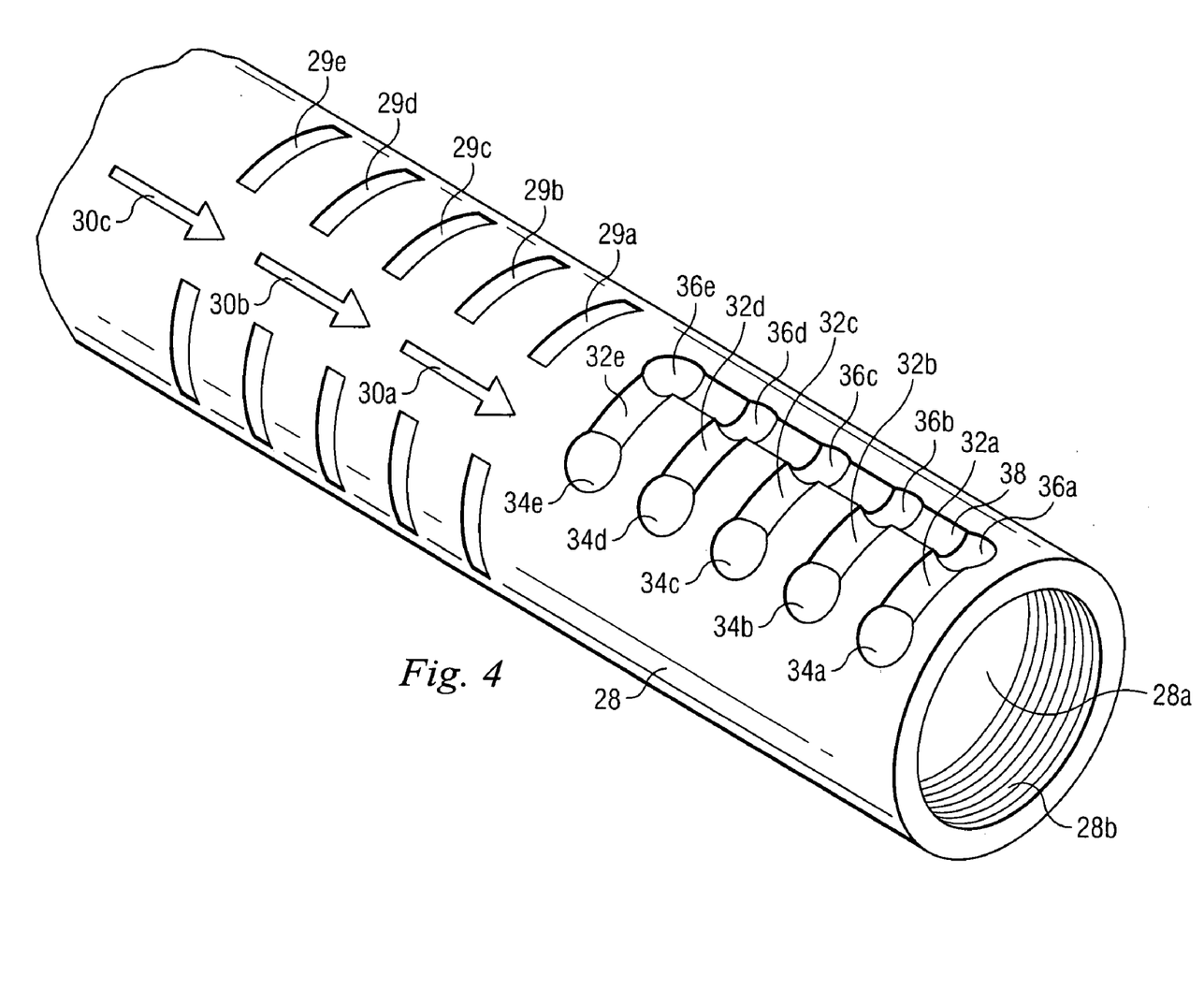
FIG. 4 is an enlarged view of a component shown in FIG. 3.

As more clearly shown in FIG. 4, locking detents 34a through 34e are formed in the tubular member 28 at the ends of the channels 32a through 32e, respectively. Likewise, positioning detents 36a through 36e are formed in the tubular member 28 at the opposing ends of the channels 32a through 32e, respectively. The depth of each detent 34a through 34e, and each detent 36a through 36e, is greater than the depth of each channel 32a through 32e, respectively. A longitudinally-extending positioning channel 38 is formed in the proximal end portion of the tubular member 28 and extends from the detent 36a to the detent 36e, passing through the detents 36b through 36d. The channel 38 is not continuous, but instead is interrupted by the detents 36a through 36e because the depth of the channel is less than the depth of each detent 36a through 36e.

Figure 3:
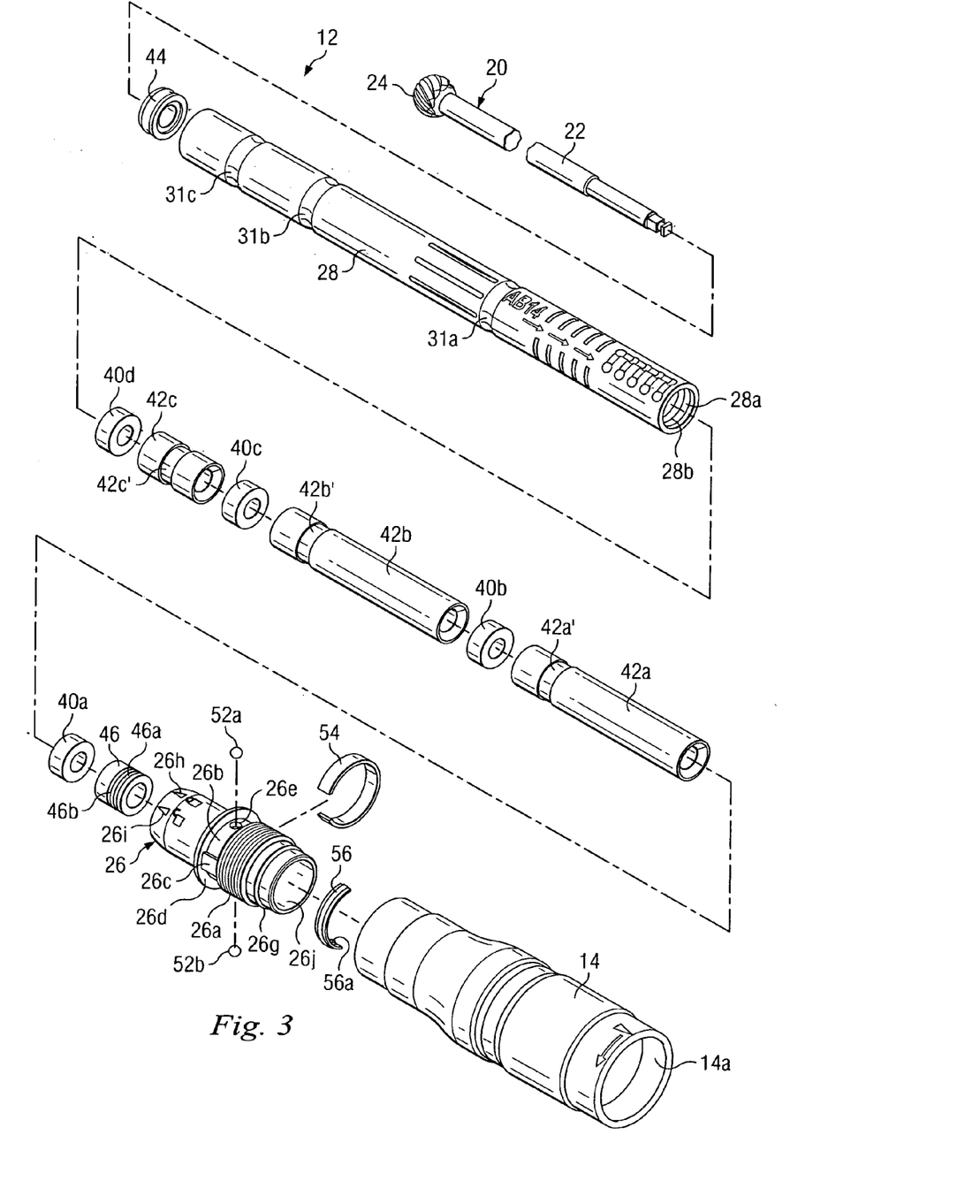
FIG. 3 is an exploded view of a portion of the dissection tool assembly of FIG. 2.

The foregoing arrangement of the channels 32a through 32e, the detents 34a through 34e, the detents 36a through 36e and the channel 38 is replicated on the surface of the tubular member 28 opposite the surface shown in FIGS. 3 and 4 so that, if the tubular member 28 shown in FIG. 4 was rotated 180 degrees, the view with respect to these replicated channels and detents would be identical to that of FIG. 4. These replicated channels and detents are referred to by corresponding prime reference numerals (the detents 34a', 34b', 34c', 34d' and 34e' are shown in FIG. 5B).

Bearing assemblies 40a, 40b, 40c and 40d are disposed in the bore 28a of the tubular member 28. Spacers 42a, 42b and 42c are also disposed in the bore 28a so that the spacer 42a is positioned between the bearing assemblies 40a and 40b, the spacer 42b is positioned between the bearing assemblies 40b and 40c, and the spacer 42c is positioned between the bearing assemblies 40c and 40d. Channels 42a', 42b' and 42c' are formed in the spacers 42a, 42b and 42c, respectively. As clearly shown in FIG. 5C, the spacers 42a through 42c are positioned in the bore 28a so that the protrusion portions of the crimps 31a, 31b and 31c extend into the channels 42a', 42b' and 42c', respectively, and lockingly engage the spacers.

A stop 44 is connected to the distal end of the tubular member 28 and a portion of the stop is positioned in the bore 28a. A plug 46 having a pair of channels 46a and 46b is positioned in the bore 28a near the proximal end of the tubular member 28 so that the channels are associated the grooves 28b. The plug 46 applies a force against the bearing assembly 40*a* and is positioned in the bore 28*a* so that, due to the fixed position of the stop 44, clamping forces are applied to the bearing assemblies 40*a* through 40*d* and the spacers 42*a* through 42*c*. The channels 46*a* and 46*b* and the grooves 28*b* are filled with an adhesive such as epoxy so that the plug 46 is fixed within the bore 28*a*, thereby maintaining the aforementioned clamping forces. The plug 46, the bearing assemblies 40*a* through 40*d*, the spacers 42*a* through 42*c* and the stop 44 form a substantially continuous bore 48 (shown in FIG. 5B).

A bore 50 of varying cross-section extends through the housing 14, from the cavity portion 14*a* and to the distal end of the housing. Balls 52*a* and 52*b* are received by the openings 26*e* and 26*f*, respectively. A keeper spring 54 is disposed in the channel 26*b* of the coupling 26 and in a channel 50*a* formed in the inner wall of the bore 50, contacting and applying inwardly-directed radial forces on the balls 52*a* and 52*b*. An arcuate member 56 partially extends about the proximal end portion of the coupling 26. The arcuate member 56 includes a tab 56*a* that is disposed in the groove 26*g*.

When the dissection tool assembly 10 is in its assembled condition shown in FIGS. 5A through 5D, the coupling 26 is disposed in the bore 50 and is threadably engaged with the housing 14 via the threaded portion 26*a* so that the distal end of the housing is adjacent to or abuts the ring 26*d*. The outer surfaces of the housing 14 and the ring 26*d* are substantially flush. It is understood that an adhesive such as epoxy may be applied to the threaded portion 16*a*. The tubular member 28 is slidably engaged with the coupling 26 so that the balls 52*a* and 52*b* are seated in the opposing detents 34*e* and 34*e'*, respectively, and the distal end of the tubular member 28 extends from the housing 14 at a predetermined distance. The outer diameter of the coupling 26 decreases from the ring 26*d* to the distal end of the coupling so that, at the distal end, the difference between the outer diameters of the coupling and the tubular member 28 is relatively small.

The shaft 22 of the dissection tool 20 extends through the bore 48 and, as discussed above, is inserted in the distal portion 16*a* of the motor 16 which, in turn, is positioned within the cavity portion 14*a* of the housing 14 (motor not shown). The dissection head 24 and the distal portion of the shaft 22 extend out from the tubular member 28. The tubular member 28 is in a "locked" position, as indicated by the alignment of the arrow marking 30*c* with the marking 26*h* shown in FIG. 5A, because the tubular member 28 is unable to move relative to the coupling 26, as will be further described in detail below.

In operation, the motor 16 receives high-pressure air via the hose assembly 18 to rotate a rotor shaft (not shown in the Figures) that is coupled with the shaft 22 of the dissection tool 20, as disclosed in detail in the above-incorporated patent application. Due to this coupling, the shaft 22 rotates, thereby rotating the dissection head 24, which may be applied against bone or other human tissue to cut or dissect the bone or tissue. Low-pressure exhaust air exits the motor 16 through an exhaust passage in the hose assembly 18.

During this time, the dissection tool assembly 10 is in its assembled condition described above and the shaft 22 rotates in the bores 48 and 50. The bearing assemblies 40*a* through 40*d* support the rotating shaft 22. Due to the above-described clamping forces, the spacers 42*a*, 42*b* and 42*c* limit any movement of the bearing assemblies 40*a* through 40*d* relative to the bore 28*b* of the tubular member 28, providing increased stability to the shaft 22.

The locking engagement of the crimps 31*a*, 31*b* and 31*c* with the channels 42*a'*, 42*b'* and 42*c'*, respectively, facilitates the binding of the wall of the bore 28*b* to the spacers 42*a*, 42*b* and 42*c*, respectively, thereby limiting any movement of the spacers relative to the bore 28*b*. This serves to better stabilize the shaft 22 while the dissection head 24 is dissecting the bone or tissue, during which time the dissection tool assembly 10 is subjected to a variety of static and/or dynamic (shock or vibrating) loads in a variety of directions. The binding of the wall of the bore 28*b* to the spacers 42*a* through 42*c* also increases the stiffness of the tubular member 28, providing increased stability to the shaft 22, especially when the coupling 26 or the tubular member 28 is subjected to static or dynamic transverse loading.

The adhesive applied to the threaded portion 26*a* prevents the coupling 26 from disengaging from the housing 14 while the dissection tool assembly 10 is undergoing the above-described static and dynamic loading. The arcuate member 56 secondarily prevents the coupling 26 from disengaging from the housing 14, as will be further described in detail below.

As noted above and during operation, the tubular member 28 is in a "locked" position where the tubular member 28 is unable to move in a longitudinal direction relative to the coupling 26, the housing 14 and the tool 20. It is understood that a "locked" position during operation of the dissection tool assembly 10 is desirable in order to prevent any unwanted axial movement of the tubular member 28, relative to the coupling 26 and the shaft 22, that might interfere with the surgeon's line of sight or the cutting operation of the dissection head 24, thereby possibly increasing the risk of harm to the human patient.

Figure 5A:
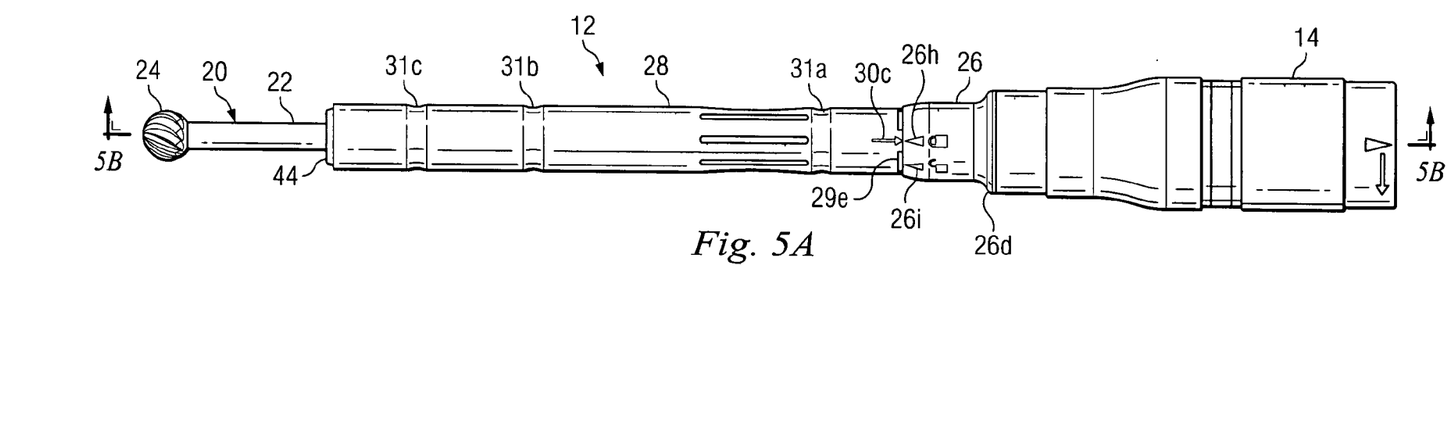
FIG. 5A is a plan view of the portion of the dissection tool assembly of FIG. 3.
Figure 5B:
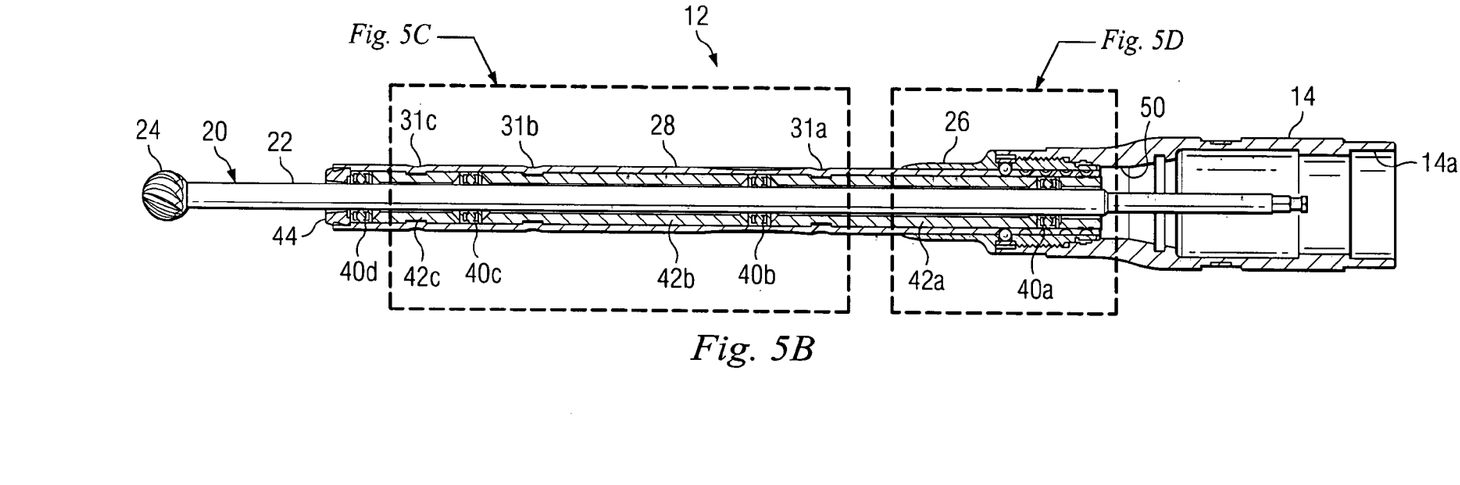
FIG. 5B is a sectional view of the portion of the dissection tool assembly of FIG. 5A taken along line 5B-5B.
Figure 5C:
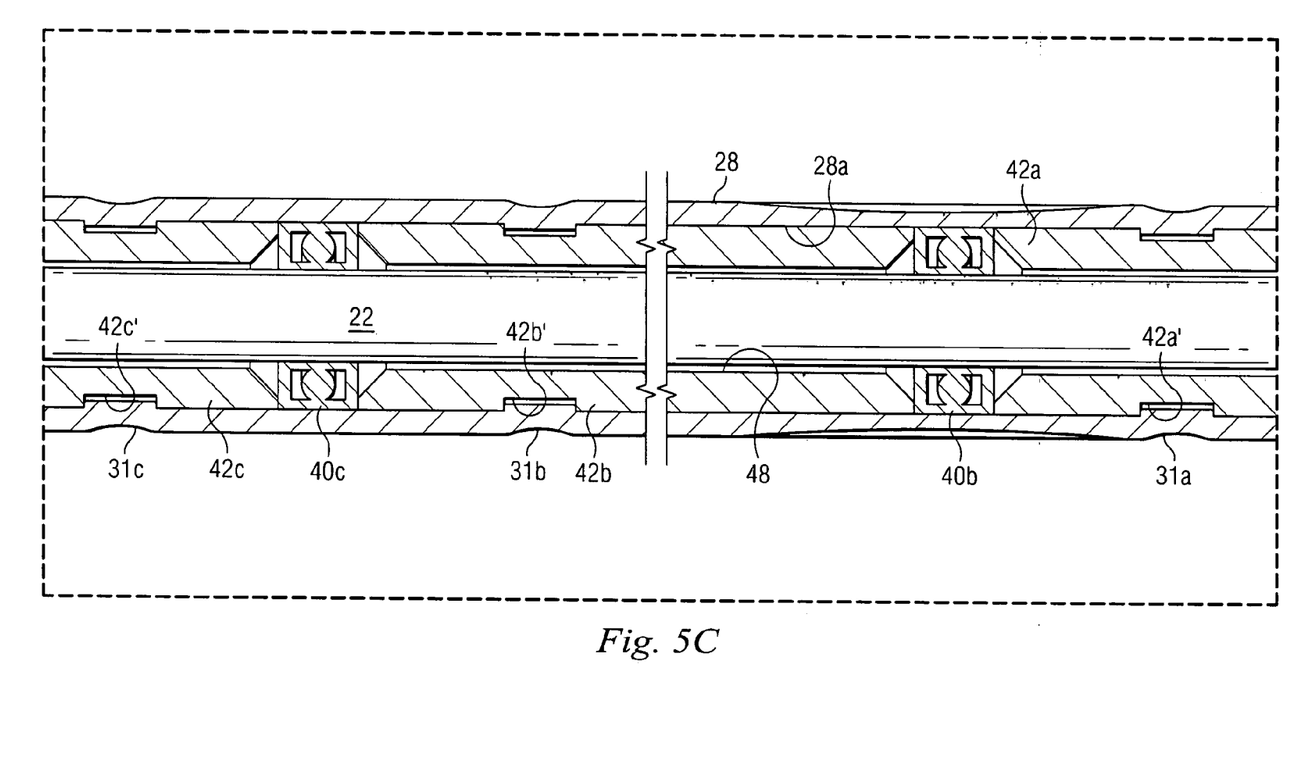
FIG. 5C is an enlarged view of a portion of the sectional view shown in FIG. 5B.
Figure 5D:
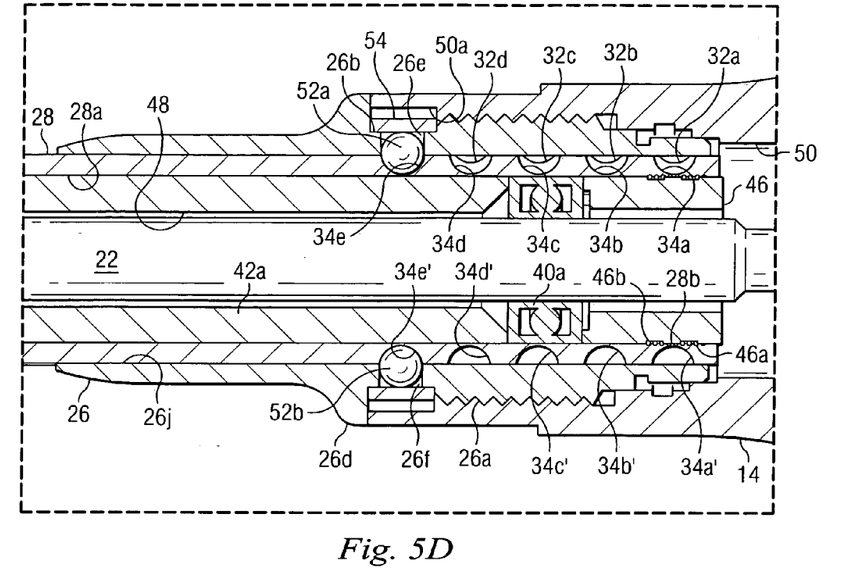
FIG. 5D is an enlarged view of another portion of the sectional view shown in FIG. 5B.

As shown in FIGS. 5B and 5D, the tubular member 28 is prevented from moving longitudinally relative to the coupling 26 because the balls 52*a* and 52*b* are seated in the detents 34*e* and 34*e'*, respectively. If the surgeon attempts to move the tubular member 28 in a direction towards the dissection head 24, the tubular member 28 will remain substantially in position due to the contact between the walls of the detents 34*e* and 34*e'* and the substantially immobile balls 52*a* and 52*b* extending through the through-openings 26*e* and 26*f*, respectively. It is understood that the tubular member 28 is prevented from moving relative to the coupling 26 when the ball 52*a* is seated in any one of the detents 34*a* through 34*e*, and the ball 52*b* is seated in any one of the detents 34*a'* through 34*e'*.

The keeper spring 54 prevents the balls 52*a* and 52*b* from falling out of the through-openings 26*e* and 26*f*, respectively. The keeper spring 54 holds the balls 52*a* and 52*b* in place due to the spring's application of inwardly-directed radial forces on the balls. The protrusion 26*c* limits the rotation of the keeper spring 54 about the coupling 26 in the channel 26*b* to the extent that the location of the split in the keeper spring 54 does not correspond to the location of the through-openings 26*e* and 26*f* (split shown in FIG. 3).

As shown in FIGS. 5A and 5B, the distal portion of the shaft 22 is exposed to view, extending out from the tubular member 28 as far as possible while remaining in a "locked" position as described above. The alignment of the distal end of the coupling 26 with the index marking 29*e* further indicates this condition of maximum shaft 22 extension and the corresponding maximum insertion of the tubular member 28 into the coupling 26. In order for the tubular member 28 to protect and/or support a greater amount of the distal portion of the shaft 22, the tubular member is moved axially in a direction towards the dissection head 24, relative to the coupling 26, the housing 14 and the tool 20.

To so move the tubular member 28, the motor 16 is adjusted so that the shaft 22 of the tool 20 ceases to rotate. The tubular member 28 is then rotated counterclockwise (as viewed in FIGS. 3 and 4) about its longitudinal axis while the coupling 26 remains stationary. Rotation of the tubular member 28 results in the rotation of the channel 32e (FIG. 5D) towards the ball 52a. The difference between the depths of the detent 34e and the channel 32e is sized so that the channel 32e is able to slide underneath the ball 52a. The keeper spring 54 resists the sliding of the channel 32e and the corresponding outwardly-directed radial movement of the ball 52a, providing tactile and/or acoustic feedback to the surgeon that indicates that the channel is indeed underneath the ball 52a. It is understood that the operation of the tubular member 28 with respect to the ball 52b, and the corresponding channels and detents referred to by prime reference numerals, is identical to the foregoing, and is also identical to the below-described operation with respect to the ball 52a, and therefore will not be described.

Figure 6A:
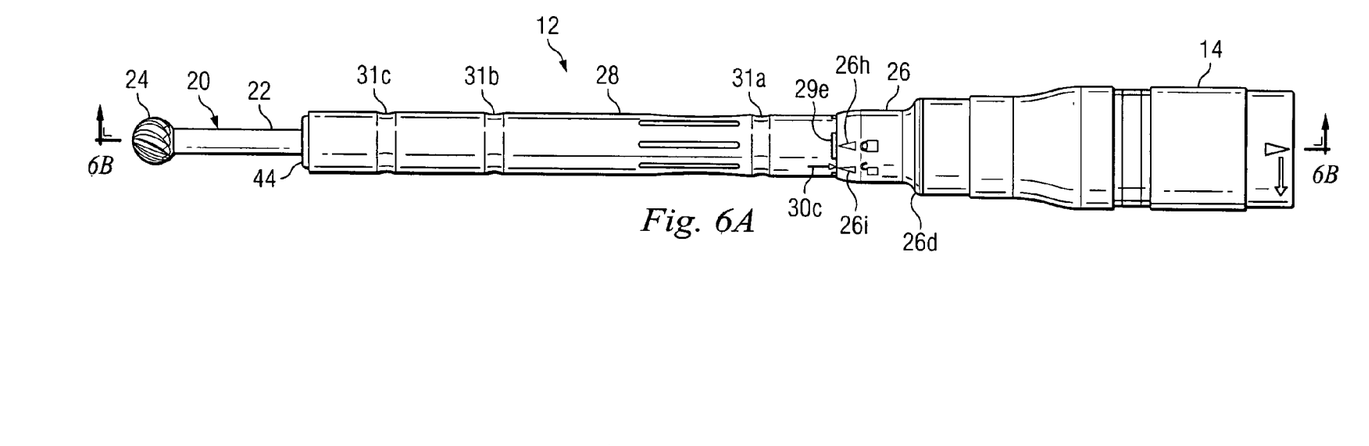
FIG. 6A is a view similar to that of FIG. 5A but depicting another operational mode.
Figure 6B:
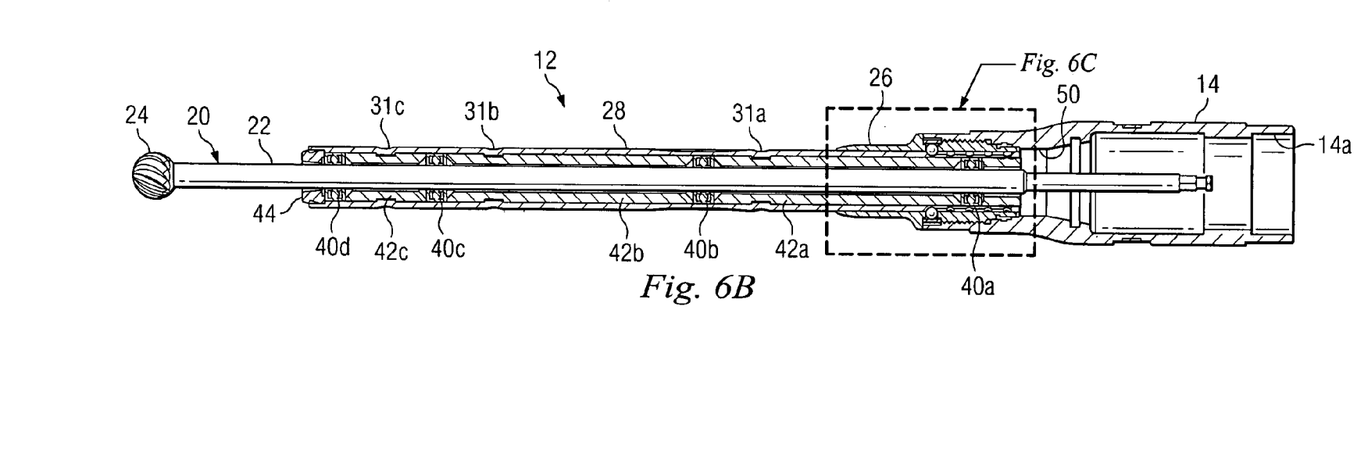
FIG. 6B is a sectional view of the portion of the dissection tool assembly of FIG. 6A taken along line 6B-6B.
Figure 6C:
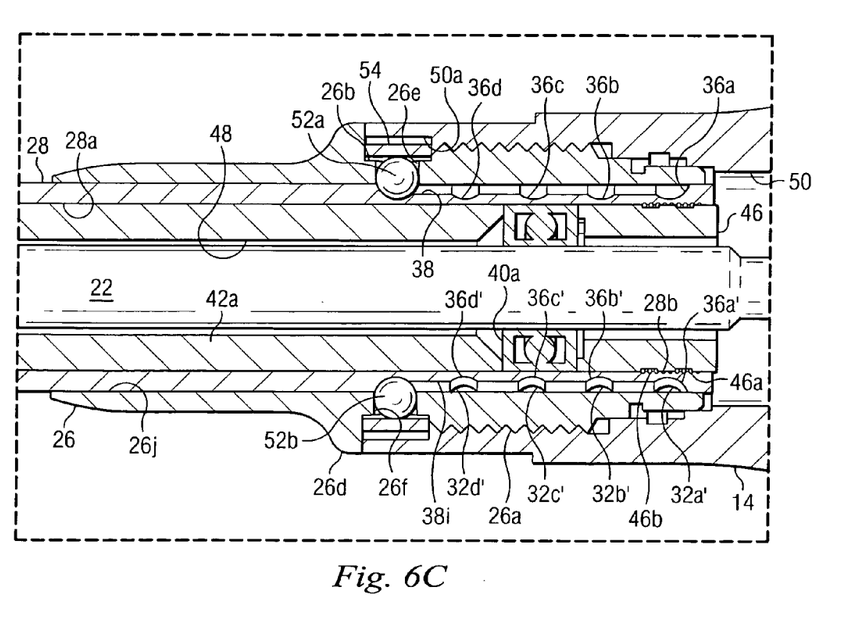
FIG. 6C is an enlarged view of a portion of the sectional view shown in FIG. 6B.

Referring to FIGS. 6A through 6C, rotation of the tubular member 28 is continued so that the channel 32e continues to slide against the ball 52a until the ball 52a falls into the detent 36e, assisted by the force applied on the ball by the keeper spring 54. The falling of the ball 52a from the channel 32e and into the detent 36e, and the corresponding decrease in loading on the keeper spring 54, provides both acoustic and tactile feedback to the surgeon, indicating that the ball is indeed in the detent 36e and in an "unlocked" position. The alignment of the arrow 30c with the marking 26i provides further confirmation of this "unlocked" position. The contact between the ball 52a and the wall of the detent 36e prevents the tubular member 28 from further counterclockwise rotation.

A longitudinally-directed force is applied to the tubular member 28 so that the tubular member is moved axially in the direction towards the dissection head 24, during which time the channel 38 slides along underneath the ball 52a. As the detents 34d, 34c and 34b also slide underneath the ball 52a during this movement, the ball drops down into each detent, providing acoustic and tactile feedback to the surgeon as to the extent of the tubular member 28's movement. The movement of the index markings 29a through 29e relative to the coupling 26 further indicates the extent of the tubular member 28's movement. The tubular member 28 continues to be moved axially until the detent 36a slides underneath the ball 52a and the ball drops into the detent. Contact between the ball 52a and the wall of the detent 36a prevents further axial movement of the tubular member 28 in the direction towards the dissection head 24.

Figure 7A:
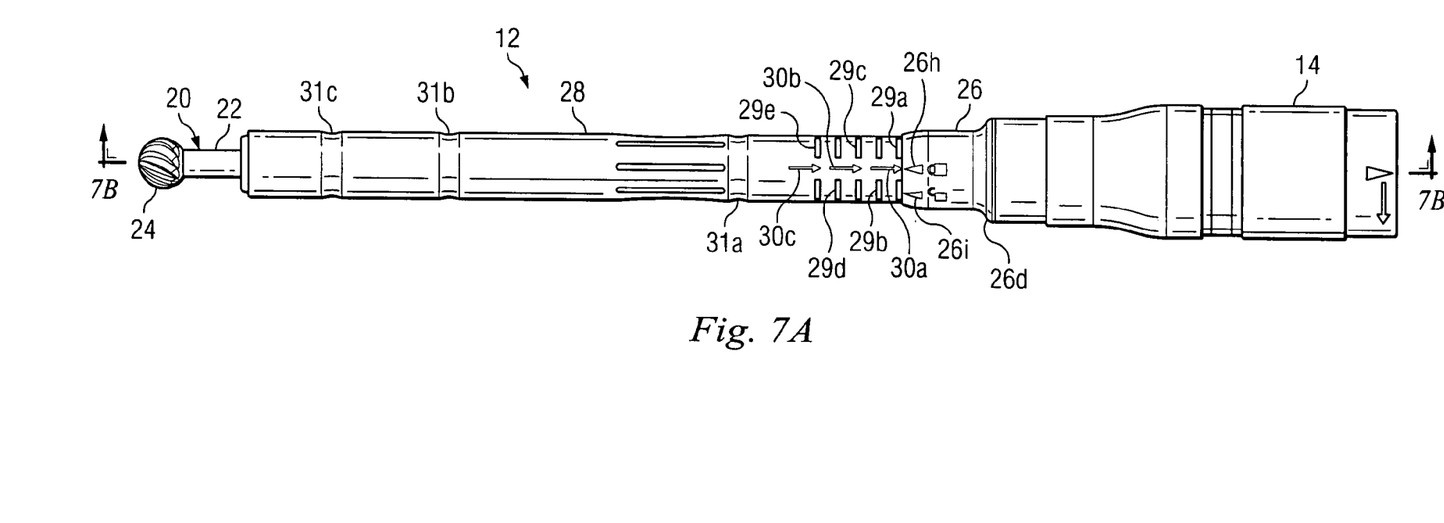
FIG. 7A is a view similar to that of FIG. 5A but depicting yet another operational mode.
Figure 7B:
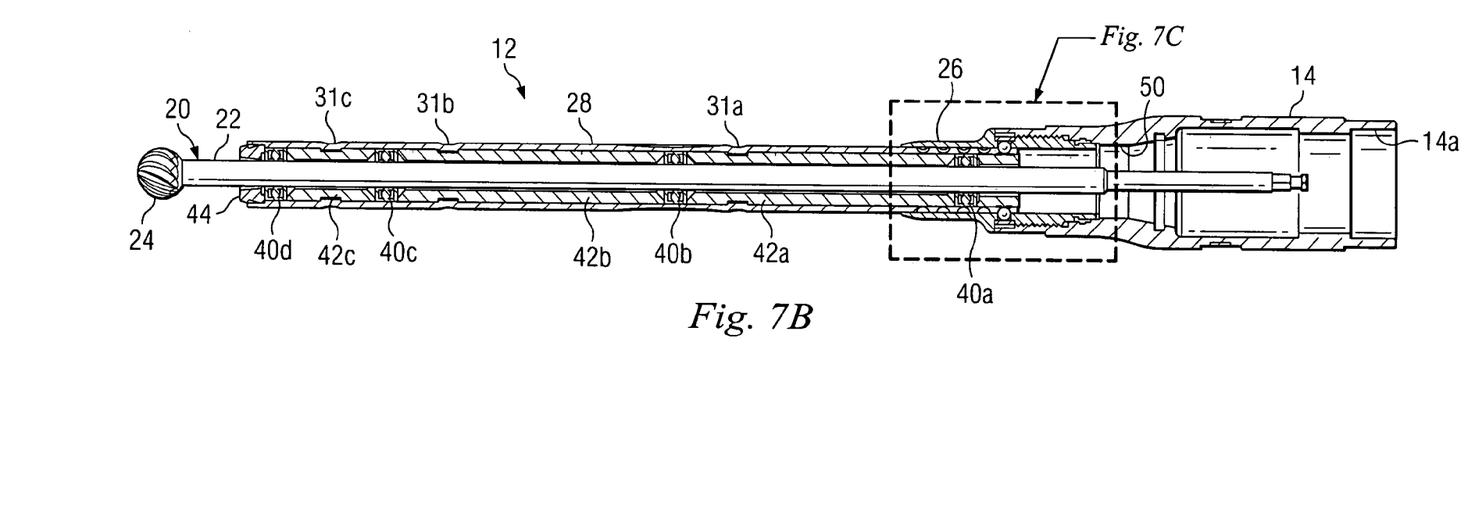
FIG. 7B is a sectional view of the portion of the dissection tool assembly of FIG. 7A taken along line 7B-7B.
Figure 7C:
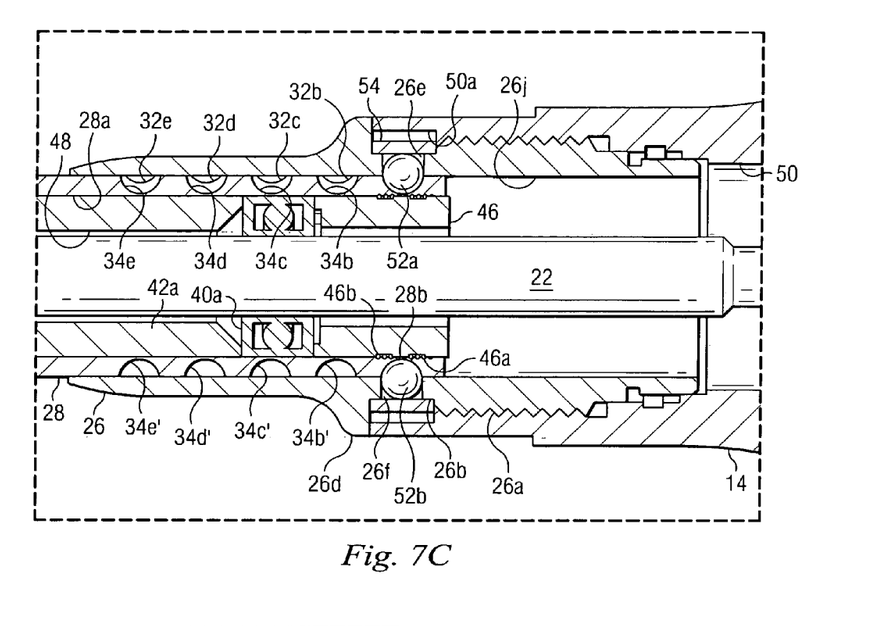
FIG. 7C is an enlarged view of a portion of the sectional view shown in FIG. 7B.
Figure 8A:
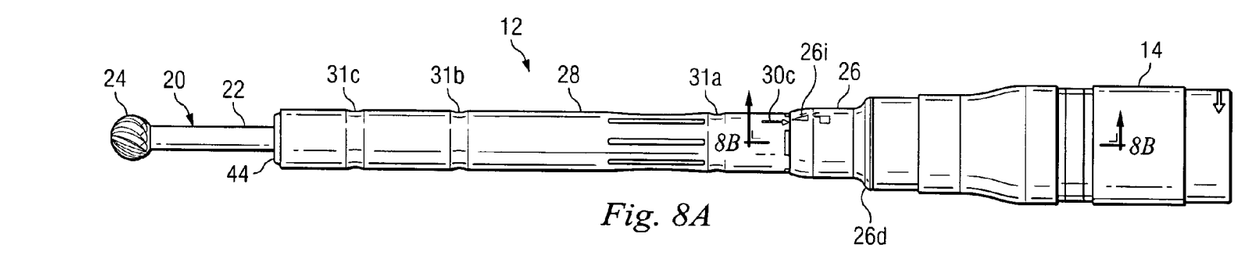
FIG. 8A is an elevation view of the portion of the dissection tool assembly of FIG. 3.
Figure 8B:
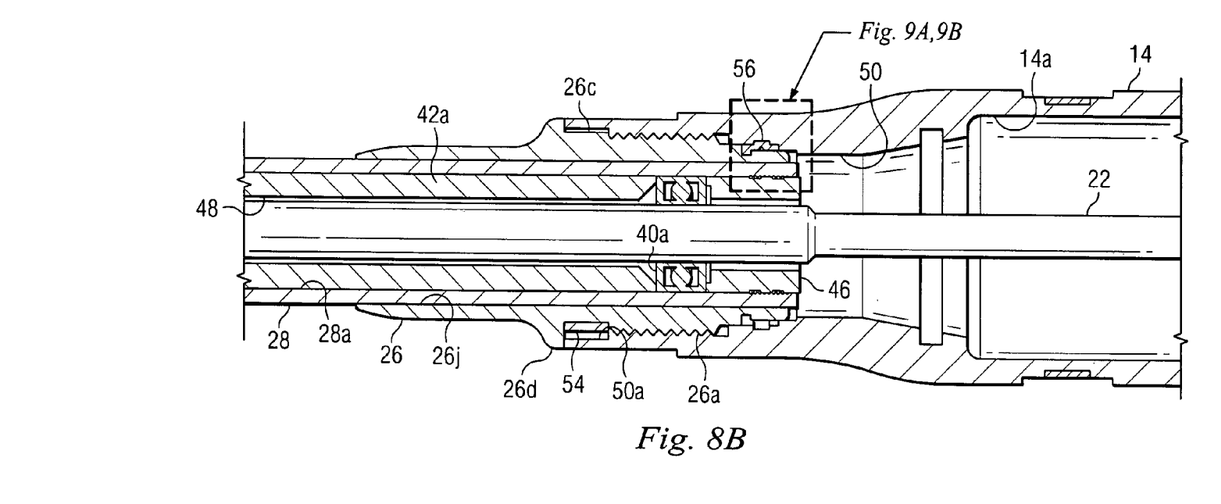
FIG. 8B is a sectional view of the portion of the dissection tool assembly of FIG. 8A taken along line 8A-8A.

The tubular member 28 is placed in a "locked" position by rotating the tubular member 28 in a clockwise direction (as viewed in FIGS. 3 and 4). During this rotation and referring to FIGS. 7A through 7C, the detent 34a rotates towards the ball 52a while the channel 32a slides underneath the ball. The ball 52a falls into the detent 34a, providing acoustic and tactile feedback to the surgeon, indicating that the ball is indeed in the detent 34a and in a "locked" position. At this point, the tubular member 28 protects and/or supports the greatest amount of the distal portion of the shaft 22 while still being in a "locked" position, as indicated by the alignment of the distal end of the coupling 26 with the index marking 29a, and the alignment of the arrow 30a with the marking 26h. Normal operation of the motor 16, and the corresponding rotation of the shaft 22 and the dissection head 24, may now resume.

Instead of axially moving the tubular member 28 until the ball 52a falls into the detent 36a, it is understood that the movement of the tubular member 28 may be stopped at any point along the channel 38. If the tubular member 28 movement is stopped when the ball 52a is located in the detents 36b, 36c and 36d, the acoustic and tactile feedback of the ball 52a falling into any one of these detents indicates to the surgeon that the tubular member 28 may be locked with respect to its current position relative to the coupling 26 and the shaft 22. The alignment of one of the index markings 29a through 29e with the distal end of the coupling 26 further indicates to the surgeon that the tubular member 28 may be placed in a "locked" position. Regardless of which detent 36a through 36e the ball 52a is seated in, the procedure for locking the tubular member 28 is identical to the above-described procedure. Further, rotation of the shaft 22 and the dissection head 24 may safely resume as long as the tubular member 28 is locked, that is, the ball 52a is seated in one of the detents 34a through 34e.

It is understood that the tubular member 28 may be unlocked in the above-described manner, moved axially in either direction with respect to the coupling 26, and then locked in the above-described manner. Thus, the tubular member 28 may be selectively adjusted so that it telescopes in and out of the coupling 26, towards and away from the dissection head 24 in discrete, repeatable, and indexed increments. Further, this selective adjustment may be carried out without an appreciable increase in the surgical attachment instrument 12's interference with the surgeon's line of sight to the surgical area. This lack of interference is due in part to the outer surfaces of the housing 14 and the ring 26d being substantially flush, and the decrease in the outer diameter of the coupling 26 from the ring to the distal end of the coupling. This lack of interference is further due in part to the positioning of the balls 52a and 52b and the keeper spring 54 within the housing 14.

As noted above, the arcuate member 56 prevents the threaded portion 26a of the coupling 26 from disengaging from the housing 14. Referring to FIGS. 8A through 9B, with continuing reference to FIG. 3, a recess 58 having walls 58a and 58b is formed in the wall of the bore 50, and a recess 60 is formed in a wall 58b of the recess 58. The recess 60 includes two walls 60a and 60b and a channel 62 is formed in the wall 60b. When the dissection tool assembly 10 is in its assembled condition, the edge of the arcuate member 56 opposing the tab 56a is contacting the wall 60a. A portion of the arcuate member 56 is crumpled and extends into the channel 62 formed in the wall 60b (most clearly shown in FIG. 9B). It is understood that the material of the arcuate member 56 is softer than the material of the coupling 26 and the housing 14.

Figure 9A:
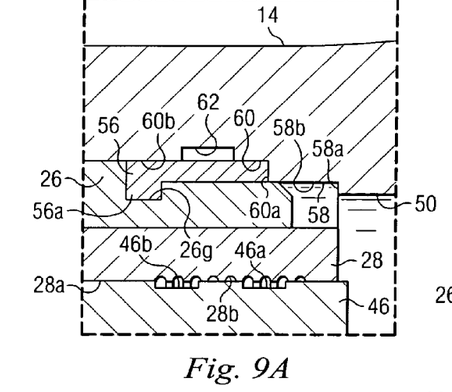
FIG. 9A is an enlarged view similar to that of a portion of the sectional view shown in FIG. 8B, but depicting a partially assembled condition between two components of the dissection tool assembly.
Figure 9B:
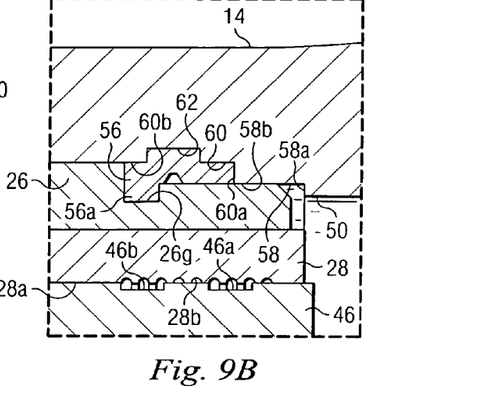
FIG. 9B is an enlarged view of a portion of the sectional view shown in FIG. 8B and is similar to the view shown in FIG. 9A, but depicting a fully assembled condition between the two components of the dissection tool assembly.

In operation, the arcuate member 56 initially has an L-shaped cross-section, before the coupling 26 is fully engaged with the housing 14, as shown in FIG. 9A. During assembly, as the coupling 26 is threadably engaged with the housing 14 via the threaded portion 26a, the proximal end of the coupling 26 moves axially towards the wall 58a and the arcuate member 56 moves towards and engages the wall 60a. The threaded engagement of the coupling 26 with the housing 14 is continued so that the proximal end of the coupling 26 continues to move towards the wall 58a. Due to the interfering engagement between the arcuate member 56 and the wall 60a, a portion of the arcuate member crumples and is forced upwards into the channel 62, as shown in FIG. 9B. During the normal operation of the dissection tool assembly 10, the threaded portion 26a of the coupling 26 is prevented from disengaging from the housing 14 due in part to the contact between the crumpled portion of the arcuate member 56 and the walls of the channel 62.

During disassembly, a predetermined amount of torque applied to the coupling 26 will either break or severely damage the arcuate member 56 so that the coupling may be disengaged from the housing 14. The partial circumferential extension of the arcuate member 56 enables the arcuate member to be easily removed from the coupling 26 and/or the channel 62. The broken or damaged arcuate member 56 may be discarded and a new arcuate member may be used when re-assembling the coupling 26 and the housing 14.

Variations

It is understood that variations may be made in the foregoing without departing from the scope of the disclosure. These variations include the following:

1. The ball 52b may be removed from the dissection tool assembly 10, along with the corresponding channels 32a' through 32e' and 38', and the detents 34a' through 34e' and 36a' through 36e'.

2. The number of balls may be increased to three or more, along with a corresponding increase in the channels and detents formed in the tubular member 28.

3. The spacers 42a through 42c may be in the form of resilient components such as elastomer or helical springs. For such embodiments, it is understood that the crimps 31a through 31c and the corresponding channels 42a' through 42c' may be removed.

4. The position of the plug 46 in the bore 28a may be varied.

5. Instead of using an adhesive in conjunction with the channels 46a and 46b and the grooves 28b, the plug 46 may be connected to the tubular member 28 by other means such as, for example, with fasteners.

6. In addition to the pneumatic motor 16, other types of motors using electricity or other motive forces may be used with the dissection tool assembly 10. It is understood that, if other types of motors are employed, the hose assembly 18 may be removed from the dissection tool assembly 10.

7. In addition to the dissection head 24, other types of dissection heads may be connected to the distal end of the shaft 22. Further, in addition to dissection heads, other types of surgical elements may be connected to the distal end of the shaft 22 such as, for example, polishing elements.

8. The number of bearing assemblies and spacers in the tubular member 28 may be varied.

9. The design of the keeper spring 54 may be modified so that there is one keeper spring engaging each ball 52a and 52b. Also, the keeper spring 54 may be in the form of other types of resilient members such as, for example, a helical spring.

10. Any foregoing spatial references, such as "upper," "between," "front," "right side," "side," "above," "beneath," etc., are for the purpose of illustration only and do not limit the specific spatial orientation of the structure described above.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to instruments and methods for telescoping an attachment tube, stabilizing a rotating shaft in connection with a dissection tool assembly, or connecting different components of a dissection tool assembly. The present invention is also not limited to instruments and associated methods for dissecting bone or other tissue per se, but may find further application in other operations such as, for example, dental procedures. The present invention further includes within its scope the methods of making, assembling and using the dissection tool assembly 10 described hereinabove.

It is intended that the scope of the disclosure be defined by the claims appended hereto and their equivalents. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A surgical attachment instrument comprising:
   a housing adapted to be coupled to a motor;
   a tubular member coupled to the housing so that an end of the tubular member extends from the housing at a predetermined distance; and
   means for selectively adjusting the predetermined distance by a repeatable increment;
   wherein the adjusting means comprises a coupling connecting the tubular member and the housing, a through-opening formed in the coupling, and a ball extending through the through-opening and engaging the tubular member;
   wherein at least two positioning detents are formed in the tubular member and longitudinally spaced at a distance corresponding to the repeatable increment for engagement by the ball;
   wherein the adjusting means further comprises a keeper spring disposed in the housing and engaged with the coupling for applying an inwardly-directed radial force to the ball;
   wherein the adjusting means further comprises a positioning channel formed in the tubular member and extending between the two positioning detents so that the tubular member moves relative to the housing in a longitudinal direction upon application of a longitudinally-directed force to the tubular member;
   wherein application of the longitudinally-directed force overcomes the inwardly-directed radial force so that the ball disengages from one of the two positioning detents and engages the positioning channel during the longitudinal movement of the tubular member;
   wherein continued application of the longitudinally-directed force causes the ball to disengage from the positioning channel and engage the other of the two positioning detents.

2. The surgical attachment instrument of claim 1 wherein further longitudinal movement of the tubular member is prevented when the ball engages the other of the two positioning detents.

3. The surgical attachment instrument of claim 1 wherein the engagement of the ball with the other of the two positioning detents provides acoustic and tactile feedback indicating that the ball has engaged the other of the two positioning detents.

4. The surgical attachment instrument of claim 1 further comprising at least two locking detents formed in the tubular member and longitudinally spaced at a distance corresponding to the repeatable increment, and at least two locking channels formed in the tubular member, each locking channel transversely-extending between each positioning detent and each corresponding locking detent.

5. The surgical attachment instrument of claim 4 wherein the tubular member rotates so that the ball disengages from one of the two positioning detents and engages the corresponding locking channel.

6. The surgical attachment instrument of the claim 5 wherein the disengagement of the ball from the one of the two positioning detents and the corresponding engagement of the ball with the corresponding locking channel provides acoustic and tactile feedback indicating that the ball has disengaged from the one of the two positioning detents.

7. The surgical attachment instrument of claim 5 wherein continued rotation of the tubular member causes the ball to disengage from the locking channel and engage the corresponding locking detent.

8. The surgical attachment instrument of claim 7 wherein further rotation of the tubular member is prevented when the ball engages the corresponding locking detent.

9. The surgical attachment instrument of claim 7 wherein the engagement of the ball with the corresponding locking detent provides acoustic and tactile feedback indicating that the ball has engaged the corresponding locking detent.

10. The surgical attachment instrument of claim 1 further comprising at least two adjacent bearing assemblies disposed in the tubular member for supporting a shaft coupled to the motor, and a spacer extending between the two adjacent bearing assemblies and lockingly engaged with the tubular member.

11. The surgical attachment instrument of claim 10 wherein the shaft rotates and wherein the locking engagement between the tubular member and the spacer stabilizes the shaft during the rotation.

12. The surgical attachment instrument of claim 1 further comprising an arcuate member concentrically disposed between the coupling and the housing, with at least a portion of the arcuate member extending in a channel formed in the housing to provide a resistance to disengagement of the coupling from the housing.

13. The surgical attachment instrument of claim 1, wherein the positioning channel and the at least two positioning detents are formed in an outer surface of the tubular member, and wherein the positioning channel has a depth that is less than a depth of the at least two positioning detents.

14. The surgical attachment instrument of claim 1, wherein the coupling is threadingly engageable with the housing.

15. The surgical attachment instrument of claim 1, wherein an inner wall of the tubular member includes a plurality of grooves for mating with a plug received within an end of the tubular member positioned within the housing.

16. The surgical attachment instrument of claim 1 further comprising means for locking the tubular member so that the tubular member is prevented from moving in a longitudinal direction relative to the housing.

17. A surgical instrument comprising:
a housing sized and shaped to be coupled to a motor;
a tubular member coupled to the housing so that a distal portion of the tubular member extends from the housing a predetermined distance, the tubular member extending generally along a longitudinal axis and comprising:
a first positioning detent formed in an outer surface of the tubular member;
a second positioning detent formed in the outer surface of the tubular member and spaced along the longitudinal axis from the first positioning detent;
a positioning channel formed in the outer surface of the tubular member and extending between the first and second positioning detents;
a first locking detent formed in the outer surface of the tubular member and substantially aligned with the first positioning detent;
a second locking detent formed in the outer surface of the tubular member and substantially aligned with the second positioning detent;
a first locking channel extending between the first positioning detent and the first locking detent in a direction substantially transverse to the longitudinal axis; and
a second locking channel extending between the second positioning detent and the second locking detent in a direction substantially transverse to the longitudinal axis; and
a coupling connecting the tubular member to the housing, the coupling comprising:
a bore extending along its length and receiving a proximal portion tubular member;
an opening extending from an outer surface of the coupling to the bore in a direction substantially transverse to the bore;
a ball extending at least partially through the opening and engaging at least one of first and second positioning detents; and
a spring engaged with the ball for applying an inwardly-directed radial force to the ball;
wherein the ball is movable between the first and second positioning detents to adjust the predetermined distance that the tubular member extends from the housing between a first predetermined distance associated with the first positioning detent and a second predetermined distance associated with the second detent, and wherein application of a longitudinally-directed force to the tubular member overcomes the inwardly-directed radial force so that the ball disengages from one of the first and second positioning detents and engages the positioning channel and wherein continued application of the longitudinally-directed force causes the ball to travel along the positioning channel and engage the other of the first and second positioning detents.

18. The surgical instrument of claim 17, wherein the ball is movable between the first positioning detent and the first locking detent to secure the tubular member at the first predetermined distance.

19. The surgical instrument of claim 18, wherein application of a rotational force to the tubular member about the longitudinal axis overcomes the inwardly-directed radial force so that the ball disengages one of the first positioning detent and the first locking detent and engages the first locking channel extending therebetween, and wherein continued application of the rotational force causes the ball to travel along the first locking channel to the other of the first positioning detent and the first locking detent.

20. The surgical instrument of claim 19, wherein the engagement of the ball with the other of the first positioning detent and the first locking detent provides acoustic and tactile feedback indicating that the ball has engaged the other of the first positioning detent and the first locking detent.

21. The surgical instrument of claim 19, wherein further rotation of the tubular member is prevented when the ball engages the other of the first positioning detent and the first locking detent.

22. The surgical instrument of claim 18, wherein the ball is movable between the second positioning detent and the second locking detent to secure the tubular member at the second predetermined distance.

23. The surgical instrument of claim 17, wherein the engagement of the ball with the other of the other of the first and second positioning detents provides acoustic and tactile feedback indicating that the ball has engaged the other of the other of the first and second positioning detents.

24. The surgical instrument of claim 17, further comprising at least two adjacent bearing assemblies disposed in the tubular member for supporting a shaft coupled to the motor, and a spacer extending between the two adjacent bearing assemblies.

25. The surgical instrument of claim 24, wherein the spacer is lockingly engaged with the tubular member.

26. The surgical instrument of claim 25, wherein the shaft rotates and wherein the locking engagement between the tubular member and the spacer stabilizes the shaft during the rotation.

27. The surgical instrument of claim 26, wherein a protrusion extends from an inner wall of the tubular member and into a channel formed in the spacer.

28. The surgical instrument of claim 17, further comprising an arcuate member concentrically disposed between the coupling and the housing, at least a portion of the arcuate member extending into a channel formed in the housing to provide a resistance to disengagement of the coupling from the housing.

29. The surgical instrument of claim 28, wherein the portion of the arcuate member is forced into the channel when the coupling moves in a longitudinal direction relative to the housing.

30. The surgical instrument of claim 29, wherein the arcuate member is comprised of material that is softer than the material of the coupling and the housing.

31. The surgical instrument of claim 30, wherein the portion of the arcuate member extending into the channel is crumpled into the channel by threading engagement of the coupling to the housing.

32. The surgical instrument of claim 28, wherein the arcuate member extends circumferentially less than 180 degrees to facilitate removal of the arcuate member after disengagement of the coupling from the housing.

33. The surgical instrument of claim 28, wherein the arcuate member is disposable.

34. A method of assembling a surgical attachment instrument, comprising:
  obtaining a housing adapted to be coupled to a motor;
  obtaining a tubular member comprising at least two positioning detents formed in an outer surface of the tubular member and longitudinally spaced along the tubular member at a fixed interval, the tubular member further comprising a positioning channel formed in the outer surface of the tubular member and extending between the at least two positioning detents;
  coupling the tubular member to the housing with a coupling element so that a distal end portion of the tubular member extends from the housing, the coupling element comprising a through-opening with a ball extending at least partially through the through-opening and a spring engaged with the housing and the ball for applying an inwardly-directed radial force to the ball, wherein coupling the tubular member to the housing comprises engaging the ball with one of the at least two positioning detents; and
  selectively adjusting how far the distal end portion of the tubular member extends from the housing by applying a longitudinally-directed force to overcome the inwardly-directed radial force so that the ball disengages from the one of the two positioning detents and engages the positioning channel during the longitudinal movement of the tubular member and wherein continued application of the longitudinally-directed force causes the ball to travel along the positioning channel and engage the other of the at least two positioning detents.

35. The method of claim 34, further comprising locking the tubular member so that the tubular member is prevented from moving in a longitudinal direction relative to the housing.

36. The method of claim 35, wherein the step of locking the tubular member comprises rotating the tubular member.

37. The method of claim 36, wherein the tubular member further comprises at least two locking detents formed in the outer surface and longitudinally spaced at the fixed interval, and at least two locking channels formed in the tubular member, each locking channel transversely-extending between each positioning detent and a corresponding locking detent, and wherein the step of locking the tubular member comprises applying a rotational force to overcome the inwardly-directed radial force so that the ball disengages from the one of the two positioning detents and engages the locking channel during the rotation of the tubular member and wherein continued application of the rotational force causes the ball to travel along the locking channel and engage the corresponding locking detent.

38. The method of claim 34, further comprising lockingly engaging the tubular member with a spacer extending between two adjacent bearing assemblies positioned within the tubular member.

39. The method of claim 34, further comprising:
  engaging an arcuate member with the coupling element; and
  threadingly engaging the coupling element with the housing to force at least a portion of the arcuate member into a channel formed in the housing, the engagement between the portion of the arcuate member and the channel resisting disengagement of the coupling from the housing.

40. The method of claim 39, wherein the portion of the arcuate member crumples into the channel formed in the housing.

41. The method of claim 34, further comprising coupling the housing to a motor.

42. The method of claim 41, further comprising inserting a shaft of a dissection tool through the tubular member and coupling the shaft to the motor.

43. The method of claim 42, wherein the step of inserting the shaft comprises inserting the shaft through at least two bearing assemblies positioned within the tubular member, the at least two bearing assemblies separated by a spacer extending therebetween and lockingly engaged with the tubular member.

44. A method of assembling a surgical attachment instrument comprising:
  providing a housing sized and shaped to be coupled to a motor, the housing comprising an inner surface defining a bore, the inner surface having a recess formed therein;
  providing a coupling element having an external threaded portion and a groove;
  positioning an arcuate member around an outer portion of a coupling element such that an inner projection of the arcuate member engages the groove of the coupling element; and
  threadingly engaging the coupling element with the housing such that, as the coupling element advances longitudinally into the bore of the housing, a portion of the arcuate member is forcibly deformed into the recess of housing, the engagement between the deformed portion of the arcuate member and the recess resisting disengagement of the coupling element from the housing.

45. The method of claim 44, further comprising:
  obtaining a tubular member comprising:

a first positioning detent formed in an outer surface of the tubular member;

a second positioning detent formed in the outer surface of the tubular member and longitudinally spaced along the tubular member from the first positioning detent; and a positioning channel formed in the outer surface of the tubular member and extending between the first and second positioning detents; and coupling the tubular member to the coupling element by engaging a ball extending at least partially through a through-opening in the coupling element with the first positioning detent;

wherein threadingly engaging the coupling element to the housing couples the tubular member to the housing so that a distal end portion of the tubular member extends from the housing.

46. The method of claim 45, further comprising selectively adjusting how far the distal end portion of the tubular member extends from the housing by applying a longitudinally-directed force to the tubular member such that the ball disengages from the first positioning detent and engages the positioning channel, and wherein continued application of the longitudinally-directed force causes the ball to travel along the positioning channel and engage the second positioning detent.

47. The method of claim 45, further comprising locking the tubular member so that the tubular member is prevented from moving in a longitudinal direction relative to the housing.

48. The method of claim 47, wherein the step of locking the tubular member comprises rotating the tubular member.

49. The method of claim 48, wherein the tubular member further comprises a first locking detent formed in the outer surface of the tubular member adjacent to the first positioning detent;

a second locking detent formed in the outer surface of the tubular member adjacent to the second positioning detent;

a first locking channel extending between the first positioning detent and the first locking detent; and a second locking channel extending between the second positioning detent and the second locking detent; and wherein the step of locking the tubular member comprises rotating the tubular member such that the ball disengages from one of the first and second positioning detents and engages the corresponding first or second locking channel, and wherein continued rotation of the tubular member causes the ball to travel along the corresponding first or second locking channel and engage the corresponding first or second locking detent.

50. The method of claim 44, further comprising lockingly engaging the tubular member with a spacer extending between two adjacent bearing assemblies positioned within the tubular member.

51. The method of claim 45, further comprising coupling the housing to a motor.

52. The method of claim 51, further comprising inserting a shaft of a dissection tool through the tubular member and coupling the shaft to the motor.

53. The method of claim 52, wherein the step of inserting the shaft comprises inserting the shaft through at least two bearing assemblies positioned within the tubular member, the at least two bearing assemblies separated by a spacer extending therebetween and lockingly engaged with the tubular member.

* * * * *